United States Patent
Kim et al.

(10) Patent No.: US 7,850,992 B2
(45) Date of Patent: Dec. 14, 2010

(54) CUCURBITURIL-CONTAINING GEL AND METHOD OF PREPARING THE SAME

(75) Inventors: Kimoon Kim, Pohang (KR); II Ha Hwang, Pohang (KR); Woo Sung Jeon, Pohang (KR); Hee Joon Kim, Pohang (KR); Dongwoo Kim, Pohang (KR); Narayanan Selvapalam, Pohang (KR); Erumaipatty R. Nagarajan, Pohang (KR)

(73) Assignees: Postech Academy-Industry Foundation, Pohang (KR); Postech Foundation, Pohang (KR)

( * ) Notice: Subject to any disclaimer, the term of this patent is extended or adjusted under 35 U.S.C. 154(b) by 957 days.

(21) Appl. No.: 11/552,624

(22) Filed: Oct. 25, 2006

(65) Prior Publication Data
US 2007/0154553 A1     Jul. 5, 2007

(30) Foreign Application Priority Data
Jan. 4, 2006     (KR) .................. 10-2006-0000892

(51) Int. Cl.
*A61K 9/14*     (2006.01)
(52) U.S. Cl. .................. 424/484; 424/85.1; 424/94.4
(58) Field of Classification Search .......... 436/507, 436/536; 514/44, 58, 183, 387, 388; 540/457, 540/472
See application file for complete search history.

(56) References Cited

U.S. PATENT DOCUMENTS

| | | | |
|---|---|---|---|
| 6,365,734 B1 * | 4/2002 | Kim et al. | 540/460 |
| 2001/0034333 A1 * | 10/2001 | Kosak | 514/44 |

FOREIGN PATENT DOCUMENTS

| | | |
|---|---|---|
| WO | 0068232 A1 | 11/2000 |
| WO | 03024978 A1 | 3/2003 |
| WO | WO 03/055888 * | 7/2003 |

OTHER PUBLICATIONS

Feihe Huang, Harry W. Gibson, Polyseudotaxanes and polyrotoxanes, Prog. Polym. Sci. 30, 982-1018, 2005.*
W.A. Freeman, et al., "Cucurbituril", J. Am. Chem. Soc., 1981, pp. 7367-7368, vol. 103, American Chemical Society.
Jaheon Kim, et al., "New Cucurbituril Homologues: Syntheses, Isolation, Characterization, and X-ray Crystal Structures of Cucurbit[n]uril (n=5, 7, and 8)", J. Am. Chem. Soc., 2000, pp. 540-541, vol. 122, American Chemical Society.

* cited by examiner

*Primary Examiner*—Michael G Hartley
*Assistant Examiner*—Jagadishwar R Samala
(74) *Attorney, Agent, or Firm*—Rothwell, Figg, Ernst & Manbeck, pc (57) ABSTRACT

Provided are a gel including a compound represented by Formula 1 below and a method of preparing the same:

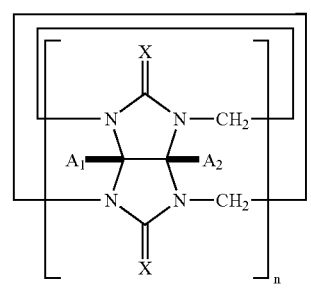

(1)

wherein $n$, $X$, $A_1$, and $A_2$ are as defined in the specification.

11 Claims, 5 Drawing Sheets

CUCURBITURIL-CONTAINING GEL AND METHOD OF PREPARING THE SAME

CROSS-REFERENCE TO RELATED PATENT APPLICATION

This application claims priority from Korean Patent Application No. 10-2006-0000892, filed on Jan. 4, 2006, in the Korean Intellectual Property Office, the disclosure of which is incorporated herein in its entirety by reference.

FIELD OF THE INVENTION

The present invention relates to a gel and a preparation method thereof, and more particularly, to a cucurbituril-containing gel and a method of preparing the same.

DESCRIPTION OF THE RELATED ART

A gel, which is an intermediate state between solid and liquid, is a jellylike material that solvent molecules are trapped inside the network of aggregates of a gel-forming agent called "gelator". A colloidal suspension that gelator molecules are dissolved in a solvent is called "sol".

Generally, a gel is prepared as follows. Gelator molecules are mixed with a solvent and the resultant mixture is heated so that the gelator molecules are completely dissolved in the solvent to obtain a sol. Then, the sol is gradually cooled to a room temperature whereupon it transforms into a gel. The heating process may be omitted according to the type of the gelator molecules.

A gel phase is obtained by an intermolecular interaction between a solvent and a gelator. A gel is classified into a polymer gel and a low-molecular-weight gel according to the molecular weight of a gelator and into an organogel and a hydrogel according to the type of a solvent.

Gel formation (gelation) occurs by a weak interaction, such as a hydrophobic interaction or a hydrogen bond, between a gelator and a solvent, and a gel is maintained in a jellylike state by an appropriate weak-interaction between a gelator and a solvent.

Generally, gelator molecules are self-assembled to form elongated fibrous structures with nanometer to micrometer thickness, and a gel is a mesh-like aggregate of the fibrous structures. At this time, the fibrous structures encompass a large number of solvent molecules. Due to such structural characteristics, a gel has a larger number of voids than other materials. Gel voids can also be filled with various materials, in addition to solvent molecules, while maintaining the structure of a gel.

Cucurbituril was first reported by R. Behrend, E. Meyer, and F. Rusche in 1905. In 1981, W. Mock and coworkers characterized the cucurbituril as a hexameric macrocyclic compound with the composition of C36H36N24O12, and elucidated the crystal structure of the cucurbituril by X-ray diffraction [J. Am. Chem. Soc. 1981, 103, 7367]. They named it cucurbit[6]uril. In early 2000, Kimoon Kim and coworkers reported the improved preparation and separation of well-known cucurbit[6]uril and its homologues, cucurbit[n]urils (n=5, 7, 8), and identified their X-ray crystal structures [J. Am. Chem. Soc. 2000, 122, 540].

Meanwhile, PCT International Publication WO 00/68232 discloses cucurbit[n]uril represented by Reference Diagram 1 below:

Reference Diagram 1 wherein n is an integer of 4 to 12.

The above-described cucurbiturils are compounds consisting of unsubstituted glycoluril monomer units.

Cucurbiturils are macrocyclic compounds and have a lipophilic cavity and two hydrophilic entrances at upper and lower portions. Thus, lipophilic interactions occur in the cavity of cucurbiturils, and hydrogen bonds, polar-polar interactions, and positive charge-polar interactions occur in the two entrances having six carbonyl groups. Therefore, cucurbiturils have retention capacity for various compounds by a very stable non-covalent linkage with these compounds. Cucurbiturils form a very stable non-covalent linkage, in particular, with compounds having a functional group such as an amino group or a carboxyl group. Based on such characteristics, studies about development of drug delivery systems using cucurbiturils have been continuously conducted.

Recently, the present inventors reported a stable non-covalent complex formation between oxaliplatin approved as an anticancer agent by the Food Drug Administration (FDA) and cucurbituril used as a drug delivery system (WO03/024978).

SUMMARY OF THE INVENTION

The present invention provides a gel including a cucurbituril homologue or derivative.

The present invention also provides a method of preparing the gel.

According to an aspect of the present invention, there is provided a gel including a compound represented by Formula 1 below:

<Formula 1> wherein n is an integer of 4 to 20;

X is O, S, or NH; and $A_1$ and $A_2$ are each independently H, OR, SR, or NHR where R is selected from the group consisting of H, substituted or unsubstituted $C_1$-$C_{30}$ alkyl, substituted or unsubstituted $C_2$-$C_{30}$ alkenyl, substituted or unsubstituted $C_2$-$C_{30}$ alkynyl, substituted or unsubstituted $C_2$-$C_{30}$ carbonylalkyl, substituted or unsubstituted $C_1$-$C_{30}$ thioalkyl, substituted or unsubstituted $C_1$-$C_{30}$ alkylthiol, substituted or unsubstituted $C_1$-$C_{30}$ hydroxyalkyl, substituted or unsubstituted $C_1$-$C_{30}$ alkylsilyl, substituted or unsubstituted $C_1$-$C_{30}$ aminoalkyl, substituted or unsubstituted $C_1$-$C_{30}$ aminoalkylthioalkyl, substituted or unsubstituted $C_5$-$C_{30}$ cycloalkyl, substituted or unsubstituted $C_2$-$C_{30}$ heterocycloalkyl, substituted or unsubstituted $C_6$-$C_{30}$ aryl, substituted or unsubstituted $C_6$-$C_{20}$ arylalkyl, substituted or unsubstituted $C_4$-$C_{30}$ heteroaryl, and substituted or unsubstituted $C_4$-$C_{30}$ heteroarylalkyl.

According to another aspect of the present invention, there is provided a method of preparing a gel, the method including: (i) dissolving the compound of Formula 1 above in a solvent to prepare a sol; (ii) adding a pharmacologically active substance to the sol of (i); and (iii) converting the resultant pharmacologically active substance-containing sol of (ii) to a gel.

According to still another aspect of the present invention, there is provided a method of preparing a gel, the method including: (i) mixing the compound of Formula 1 above with a pharmacologically active substance; (ii) adding a solvent to the resultant mixture of (i) to prepare a sol; and (iii) converting the sol of (ii) to a gel.

According to yet another aspect of the present invention, there is provided a method of preparing a gel, the method including: (i) dissolving the compound of Formula 1 above in a solvent to prepare a sol; (ii) adding a stimulus-responsive compound to the sol of (i); and (iii) converting the resultant stimulus-responsive compound-containing sol of (ii) to a gel.

According to a further aspect of the present invention, there is provided a method of preparing a gel, the method including: (i) mixing the compound of Formula 1 above with a stimulus-responsive compound; (ii) adding a solvent to the resultant mixture of (i) to prepare a sol; and (iii) converting the sol of (ii) to a gel.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

The present invention provides a gel including a compound represented by Formula 1 below, i.e., a cucurbituril homologue or derivative:

<Formula 1> wherein n is an integer of 4 to 20;

X is O, S, or NH; and $A_1$ and $A_2$ are each independently H, OR, SR, or NHR where R is selected from the group consisting of H, substituted or unsubstituted $C_1$-$C_{30}$ alkyl, substituted or unsubstituted $C_2$-$C_{30}$ alkenyl, substituted or unsubstituted $C_2$-$C_{30}$ alkynyl, substituted or unsubstituted $C_2$-$C_{30}$ carbonylalkyl, substituted or unsubstituted $C_1$-$C_{30}$ thioalkyl, substituted or unsubstituted $C_1$-$C_{30}$ alkylthiol, substituted or unsubstituted $C_1$-$C_{30}$ hydroxyalkyl, substituted or unsubstituted $C_1$-$C_{30}$ alkylsilyl, substituted or unsubstituted $C_1$-$C_{30}$ aminoalkyl, substituted or unsubstituted $C_1$-$C_{30}$ aminoalkylthioalkyl, substituted or unsubstituted $C_5$-$C_{30}$ cycloalkyl, substituted or unsubstituted $C_2$-$C_{30}$ heterocycloalkyl, substituted or unsubstituted $C_6$-$C_{30}$ aryl, substituted or unsubstituted $C_6$-$C_{20}$ arylalkyl, substituted or unsubstituted $C_4$-$C_{30}$ heteroaryl, and substituted or unsubstituted $C_4$-$C_{30}$ heteroarylalkyl.

The gel according to the present invention can be prepared by dissolving the compound of Formula 1 above used as a gelator in an appropriate solvent.

In the compound of Formula 1 above, A1 or A2 may be an allyloxy group.

In the compound of Formula 1 above, n may be 7, X may be O, and A1 and A2 may be each H.

The gel of the present invention may include 1-10 wt % of the compound of Formula 1 above.

A solvent that can be used in preparation of the gel of the present invention may be distilled water, an acidic solution, a basic solution, etc.

In the present invention, gelation using the compound of Formula 1 above is more efficiently promoted in the presence of an acid or a base than in the absence of an acid or a base. For example, in the absence of an acid or a base, gelation occurs about one day after a cucurbituril used as a gelator is dissolved in a solvent. On the other hand, in the presence of an appropriate acid or base, gelation occurs immediately or in a short time after a cucurbituril used as a gelator is dissolved in a solvent.

Examples of an acid that can be used herein include an inorganic acid such as sulfuric acid, hydrochloric acid, nitric acid, phosphoric acid, chloric acid, HBF4, or HPF6; an organic acid such as acetic acid, trifluoroacetic acid, oxalic acid, benzoic acid, or ascorbic acid; and a metal-containing acid such as HAuCl4.

Examples of a base that can be used herein include an inorganic base such as sodium hydroxide, potassium hydroxide, or calcium hydroxide; and an organic base such as ammonia, methylamine, ethylamine, pyridine, or aniline.

The gel according to the present invention may further include a pharmacologically active substance. A pharmacologically active substance-containing gel can be prepared by (i) non-covalently attaching a pharmacologically active substance into a cavity of a cucurbituril homologue or derivative molecule and dissolving the resultant non-covalent complex in a solvent or (ii) dissolving a pharmacologically active substance in a solvent and dissolving a cucurbituril homologue or derivative in the resultant solution.

A pharmacologically active substance that can be used herein is not particularly limited provided that it has pharmacological activity and can be dissolved or dispersed in a solvent used in gel preparation. For example, the pharmacologically active substance may be an organic compound, a protein, a gene, etc.

Examples of the organic compound include, but are not limited to, hydrocortisone, prednisolone, spironolatone, testosterone, megestrol acetate, danasol, progesterone, indometasine, amphotericin B, and a combination thereof.

Examples of the protein include, but are not limited to, human growth hormone, G-CSF (granulocyte colony-stimulating factor), GM-CSF (granulocyte-macrophage colony-stimulating factor), erythropoietin, vaccine, antibody, insulin, glucagon, calcitonin, ACTH (adrenocorticotropic hormone), somatostatin, somatotropin, somatomedin, parathormone, thyroxine, a substance secreted from hypothalamus, prolactin, endorphin, VEGF (vascular endothelial growth factor), enkephalin, vasopressin, nerve growth factor, non-naturally occurring opioid, interferon, asparaginase, alginase, superoxide dismutase, trypsin, chymotrypsin, pepsin, and a combination thereof.

The gel according to the present invention may further include a stimulus-responsive compound. As used herein, the term "stimulus-responsive compound" refers to a compound that controls the formation and break-up of a gel in response to an external stimulus, such as light, an electrochemical stimulus, or pH change. For example, the stimulus-responsive compound may include a portion undergoing a change in structure or oxidation state under an applied electrochemical voltage, a temperature change, or a pH change.

A light-responsive compound may be a compound including an azobenzene group or a stilbene group, and an electrochemical stimulus-responsive compound may be quinone, benzoquinone, naphthoquinone, anthraquinone, hydroquinone, catechol, viologen, or a compound including one of these. A stimulus-responsive compound-containing gel is referred to as "stimulus-responsive gel".

A stimulus-responsive gel can be prepared by (i) non-covalently attaching a stimulus-responsive compound into the cavity of a cucurbituril homologue or derivative molecule and dissolving the resultant non-covalent complex in a solvent or (ii) dissolving a stimulus-responsive compound in a solvent and dissolving a cucurbituril homologue or derivative in the resultant solution.

The gel according to the present invention may also include both a stimulus-responsive compound and a pharmacologically active substance. In this case, the gel is used as a stimulus-responsive drug-release gel capable of releasing a pharmacologically active substance in response to an external stimulus, such as light, temperature change, or pH change.

The present invention also provides a method of preparing a gel including a cucurbituril homologue or derivative of Formula 1 below:

<Formula 1> wherein n, X, $A_1$, and $A_2$ are as defined above.

More specifically, the present invention provides a method of preparing a gel, the method including: (i) dissolving the compound of Formula 1 above in a solvent to prepare a sol; (ii) adding a pharmacologically active substance to the sol of (i); and (iii) converting the resultant pharmacologically active substance-containing sol of (ii) to a gel. In this case, in (i) or (ii), a stimulus-responsive compound may further be added.

The present invention also provides a method of preparing a gel, the method including: (i) mixing the compound of Formula 1 above with a pharmacologically active substance; (ii) adding a solvent to the resultant mixture of (i) to prepare a sol; and (iii) converting the sol of (ii) to a gel. In this case, in (i) or (ii), a stimulus-responsive compound may further be added.

The present invention also provides a method of preparing a gel, the method including: (i) dissolving the compound of Formula 1 above in a solvent to prepare a sol; (ii) adding a stimulus-responsive compound to the sol of (i); and (iii) converting the resultant stimulus-responsive compound-containing sol of (ii) to a gel. In this case, in (i) or (ii), a pharmacologically active substance may further be added.

The present invention also provides a method of preparing a gel, the method including: (i) mixing the compound of Formula 1 above with a stimulus-responsive compound; (ii) adding a solvent to the resultant mixture of (i) to prepare a sol; and (iii) converting the sol of (ii) to a gel. In this case, in (i) or (ii), a pharmacologically active substance may further be added.

The solvent used in the gel preparation method of the present invention may be distilled water, an acidic solution, or a basic solution, preferable examples of which are as illustrated above.

The addition order of the compound of Formula 1 above, the pharmacologically active substance, and/or the stimulus-responsive compound is not an important factor in the gel preparation method of the present invention.

The structure of a gel prepared according to the above-described method can be determined by Atomic Force Microscopy (AFM) or Scanning Electron Microscopy (SEM). That is, a droplet of a sol obtained by heating a gel is dropped on a plate and cooled to a room temperature, and the structure of the resultant gel is determined by AFM or SEM.

Hereinafter, the present invention will be described more specifically with reference to the following working examples.

EXAMPLE 1

Preparation of Cucurbituril-containing Gels (1) 0.1 mL of distilled water was added to 10 mg of cucurbit[7]uril and the resultant mixture was heated so that the cucurbit[7]uril was completely dissolved in the distilled water. The resultant sol-phase composition was cooled to a room temperature and incubated for one day to produce a gel. The gel exhibited a thermally reversible gel-sol phase transition in such a manner that gel-to-sol transition occurred by heating and sol-to-gel transition occurred by cooling to a room temperature.

Figure 1:
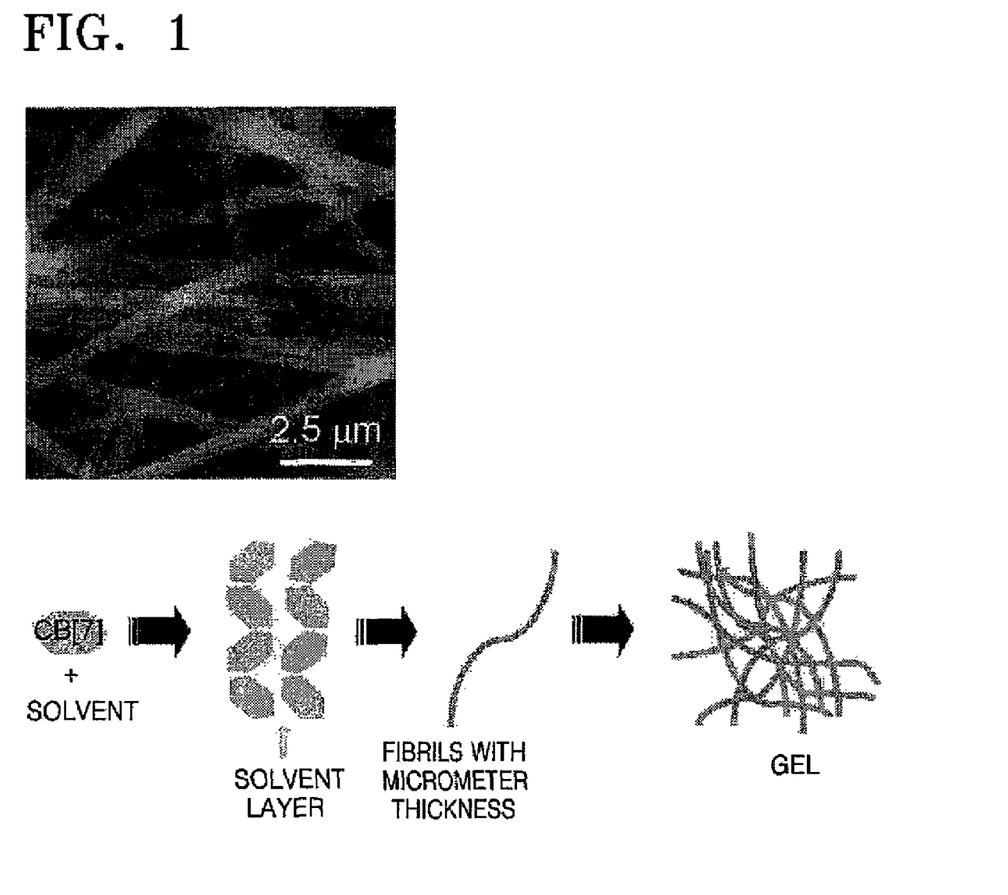
FIG. 1 is an Atomic Force Microscopic (AFM) image of the gel phase of a composition prepared by dissolving cucurbit[7]uril in an aqueous sulfuric acid solution and a schematic diagram illustrating a gel-forming process.
Figure 2:
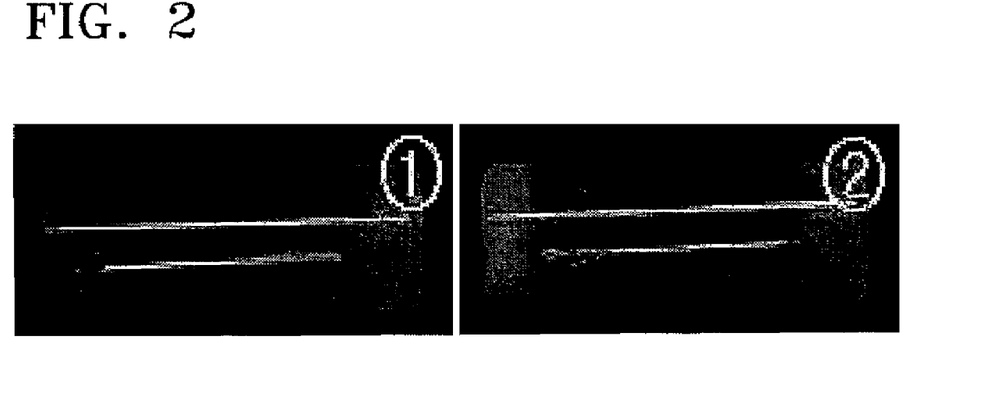
FIG. 2 is images of the sol and gel phases of a composition prepared by dissolving cucurbit[7]uril in distilled water.
Figure 3:
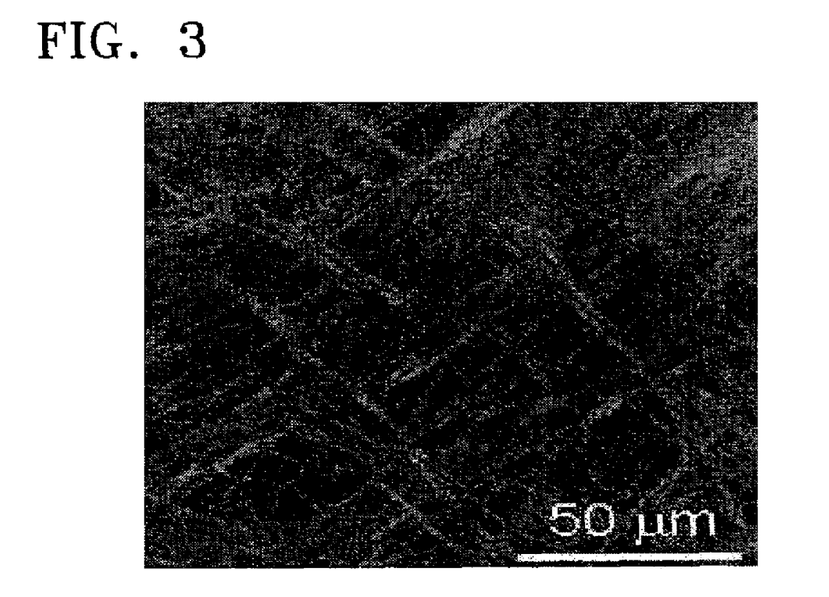
FIG. 3 is an AFM image of the gel phase of a composition prepared by dissolving cucurbit[7]uril in distilled water.

FIG. 2 is images of the sol (①) and gel (②) phases of the composition prepared by dissolving cucurbit[7]uril in distilled water, and FIG. 3 is an AFM image of the gel phase of the composition prepared by dissolving cucurbit[7]uril in distilled water.

(2) 0.2 mL of distilled water was added to 10 mg of cucurbit[7]uril and the resultant mixture was heated so that the cucurbit[7]uril was completely dissolved in the distilled water to produce a sol-phase composition. Then, 0.01 mL of a concentrated sulfuric acid (18 M) was added to the sol-phase composition, and the resultant mixture was incubated to reach a room temperature. As a result, a gel was produced within 10 minutes after the incubation. The gel exhibited a thermally reversible gel-sol phase transition in such a manner that gel-to-sol transition occurred by heating and sol-to-gel transition occurred by cooling to a room temperature.

Figure 4:
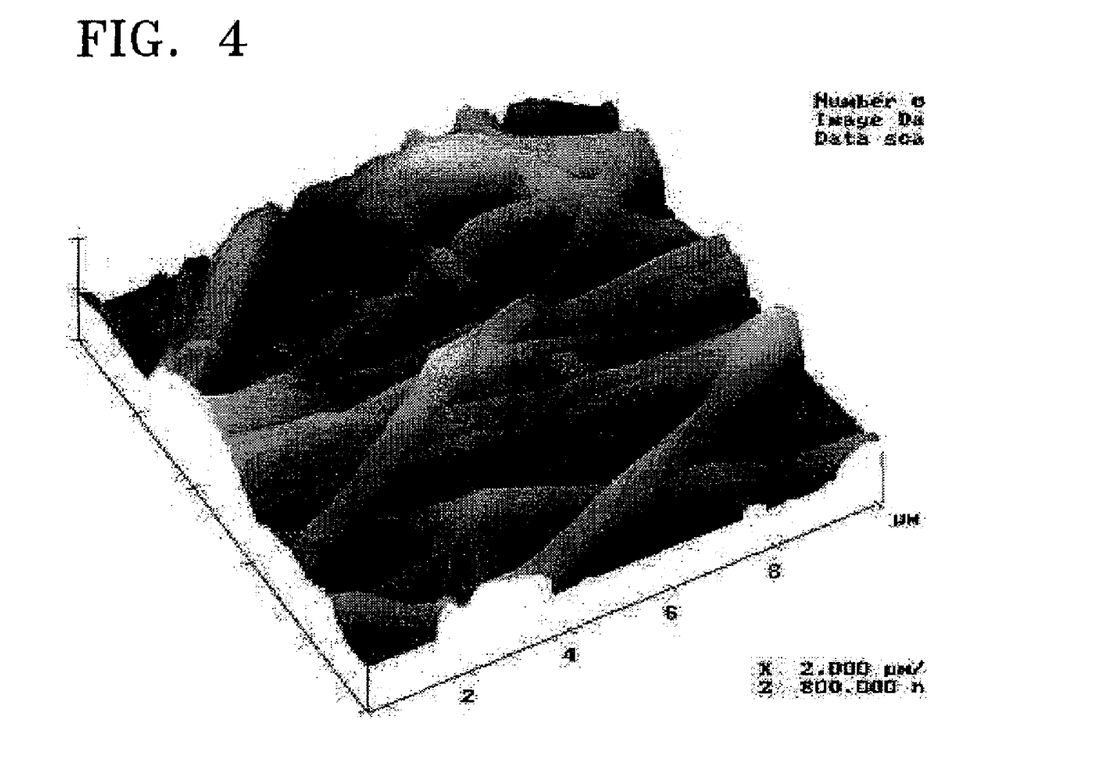
FIG. 4 is an AFM image of the gel phase of a composition prepared by dissolving cucurbit[7]uril in distilled water followed by addition of a concentrated sulfuric acid.

A droplet of a sol obtained by heating the gel was dropped on a plate and cooled, and the structure of the resultant gel was observed using an AFM. The AFM image is shown in FIG. 4. Referring to FIG. 4, the gel was in the form of an aggregate of fibrils with micrometer thickness.

(3) 0.2 mL of a 1 M sulfuric acid solution was added to 10 mg of cucurbit[7]uril and the resultant mixture was heated so that the cucurbit[7]uril completely dissolved in the sulfuric acid solution. The resultant sol-phase composition was incubated to reach a room temperature. As a result, a gel was produced within 10 minutes after the incubation.

(4) 0.2 mL of a 1 M sodium hydroxide solution was added to 10 mg of cucurbit[7]uril and the resultant mixture was heated so that the cucurbit[7]uril was completely dissolved in the sodium hydroxide solution. The sol-phase composition was incubated to reach a room temperature. As a result, a gel was produced within 10 minutes after the incubation.

EXAMPLE 2

Gel Formation and Break-up Using Temperature Change 2.5 mL of a 0.1 M sulfuric acid solution was added to 100 mg of cucurbit[7]uril and the resultant mixture was heated so that the cucurbit[7]uril was completely dissolved in the sulfuric acid solution. The resultant sol-phase composition was placed in a UV cell, and the absorbance or transmittance of the composition with respect to a temperature was measured to investigate a gelation process.

Figure 5:
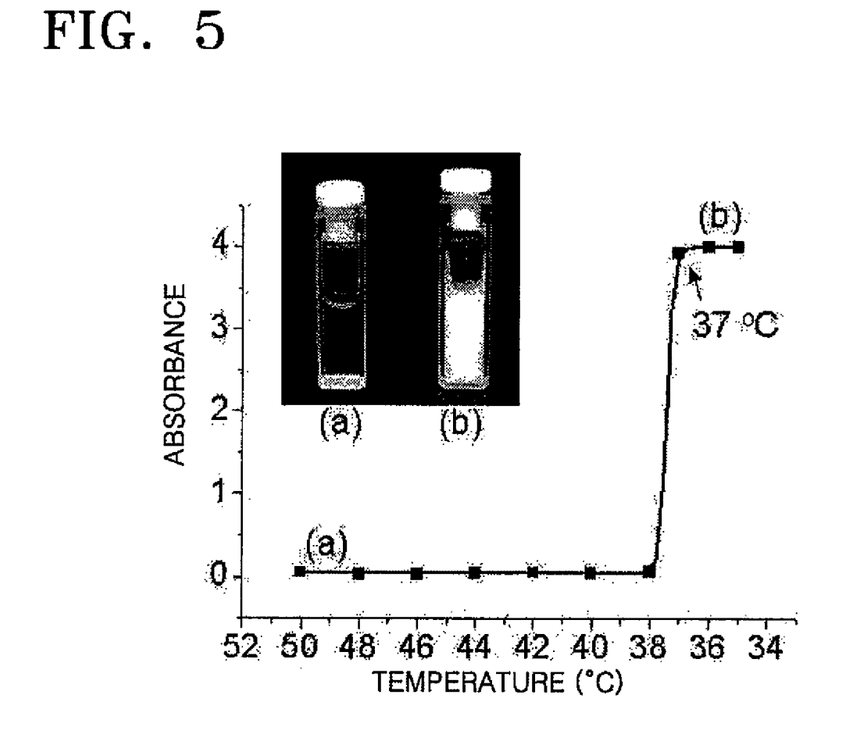
FIG. 5 is a graph illustrating an absorbance with respect to a temperature for a composition prepared by dissolving cucurbit[7]uril in a sulfuric acid solution.

In detail, the sol-phase composition was heated to 50° C. and an absorbance (800 nm) with respect to a temperature was then measured while gradually cooling down. The results are shown as a photographic image and a graph in FIG. 5. The graph of FIG. 5 shows a rapid absorbance increase (transmittance decrease) at 37° C. Such an absorbance change reveals that gelation has occurred.

In FIG. 5, the phases of (a) and (b) of the graph respectively correspond to those of (a) and (b) of the photographic image.

EXAMPLE 3

Figure 6:
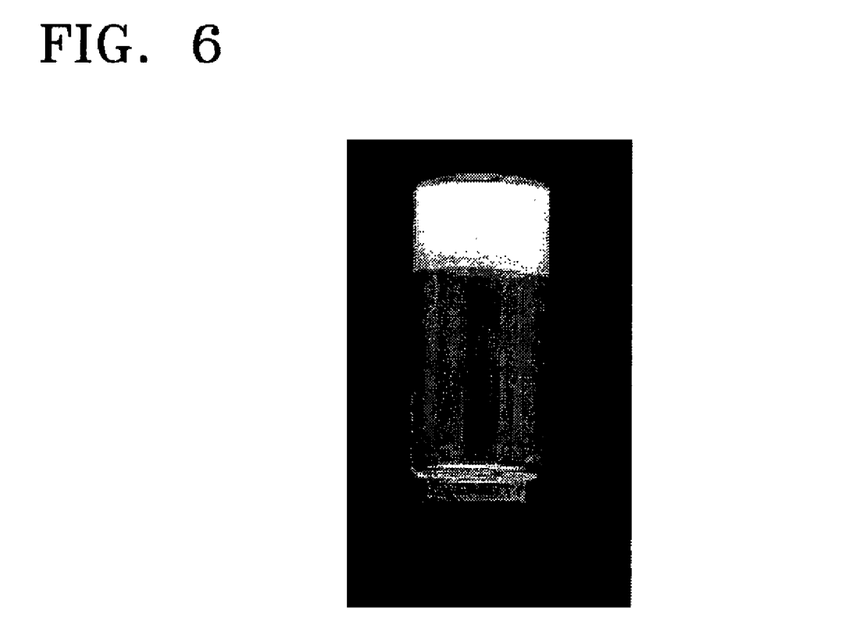
FIG. 6 is an image of the gel phase of a composition prepared by dissolving cucurbit[7]uril in a sulfuric acid solution followed by addition of oxaliplatin.

Preparation of Pharmacologically Active Substance-containing Gel 0.2 mL of a 1 M sulfuric acid solution was added to 10 mg of cucurbit[7]uril and the resultant mixture was heated so that the cucurbit[7]uril was completely dissolved in the sulfuric acid solution. The resultant solution was incubated to reach a room temperature to produce a gel. The gel was heated to obtain a sol. 0.2 eq. of oxaliplatin as a pharmacologically active substance was completely dissolved in the sol, and the resultant mixture was then incubated to reach a room temperature to produce an oxaliplatin-containing gel. FIG. 6 is an image of the oxaliplatin-containing gel.

EXAMPLE 4

Preparation of Light-responsive Molecule-containing Gel 0.2 mL of a 1 M sulfuric acid solution was added to 10 mg of cucurbit[7]uril and the resultant mixture was heated so that the cucurbit[7]uril was completely dissolved in the sulfuric acid solution. The resultant solution was incubated to reach a room temperature to produce a gel. The gel was heated to obtain a sol. 0.1 eq. of trans-diaminostilbene undergoing a cis-trans transition in response to light was completely dissolved in the sol to produce a trans-diaminostilbene-containing gel undergoing a sol-gel transition in response to light.

Figure 7:
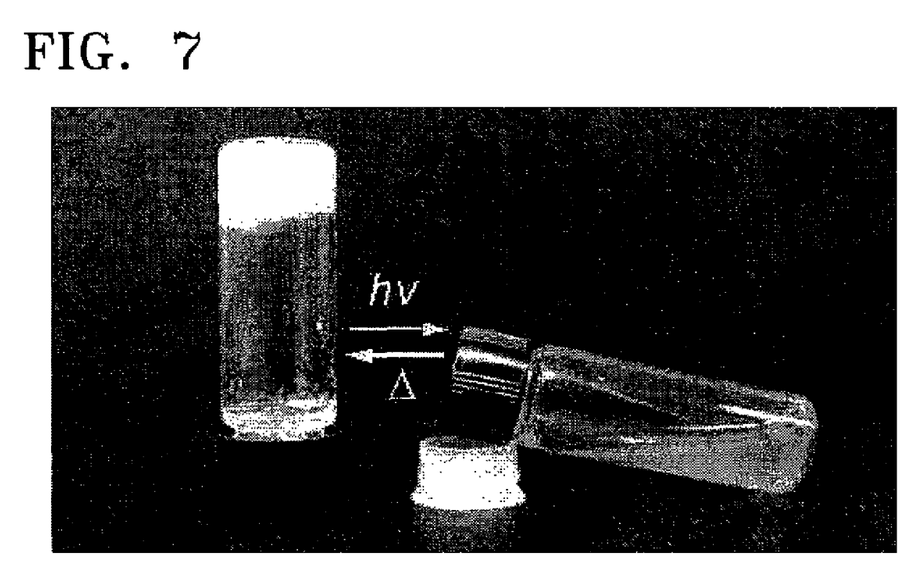
FIG. 7 is images of the sol and gel phases of a composition prepared by dissolving cucurbit[7]uril in a sulfuric acid solution followed by addition of trans-diaminostilbene.

The trans-diaminostilbene-containing gel was exposed to 350 nm UV light for one hour to obtain a sol (see FIG. 7). Such a gel-to-sol transition can be explained by the presumption that trans-diaminostilbene is converted to cis-diaminostilbene in the presence of UV light, and the cis-diaminostilbene hinders an intermolecular interaction playing an important role in gelation.

FIG. 7 shows that a color change has occurred upon gel-to-sol transition in the presence of 350 nm UV light. This can be explained by conversion of trans-diaminostilbene to cis-diaminostilbene in the presence of UV light.

Meanwhile, the cis-diaminostilbene-containing sol was converted to a gel in the presence of heat or long-wavelength (400 nm or more) light.

EXAMPLE 5

Preparation of Electrochemical Stimulus-responsive Gel 0.2 mL of a 0.5 M sulfuric acid solution was added to 10 mg of cucurbit[7]uril and the resultant mixture was heated so that the cucurbit[7]uril was completely dissolved in the sulfuric acid solution. The resultant solution was incubated to reach a room temperature to produce a gel. The gel was heated to obtain a sol. 0.7 eq. of benzoquinone undergoing an electrochemical redox reaction was completely dissolved in the sol, and the resultant mixture was then incubated to reach a room temperature to produce an electrochemical stimulus-responsive gel.

Figure 8:
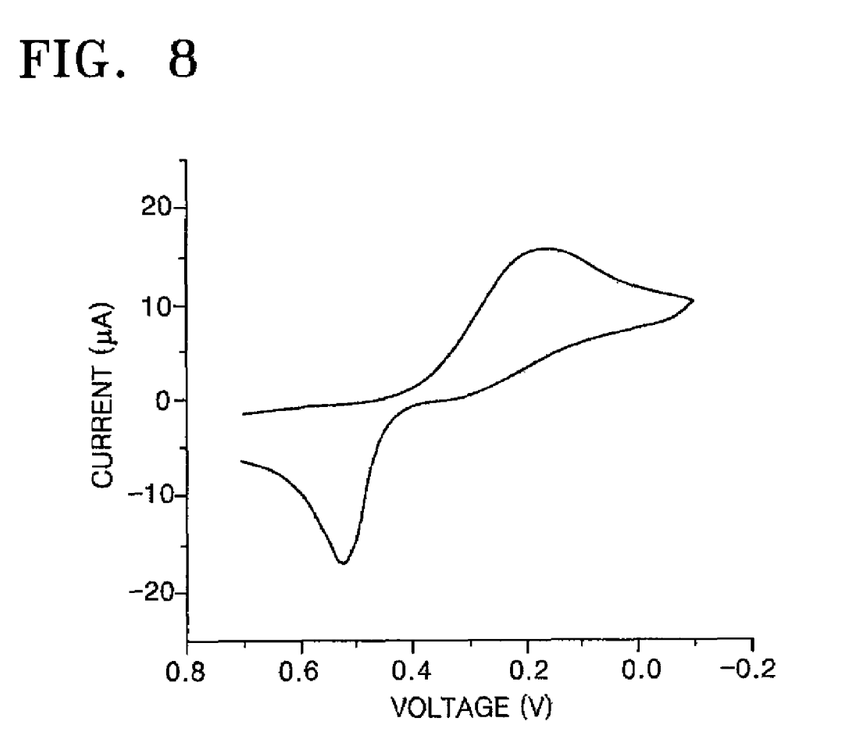
FIG. 8 is a cyclic voltammogram showing a sol-gel phase transition in response to a electrochemical stimulus for a composition prepared by dissolving cucurbit[7]uril in a sulfuric acid solution followed by addition of benzoquinone.

Cyclic voltammetry for the gel was performed using a Saturated Calomel Electrode (SCE) as a reference electrode, and the cyclic voltammogram is shown in FIG. 8.

When a voltage of −0.1 V was applied to a sol obtained by heating the gel, sol-to-gel transition occurred. This can be explained as follows. That is, benzoquinone hindering gelation is converted to hydroquinone under an electrochemical stimulus, and thus, an intermolecular interaction playing an important role in gelation is increased or hardly hindered.

Figure 9:
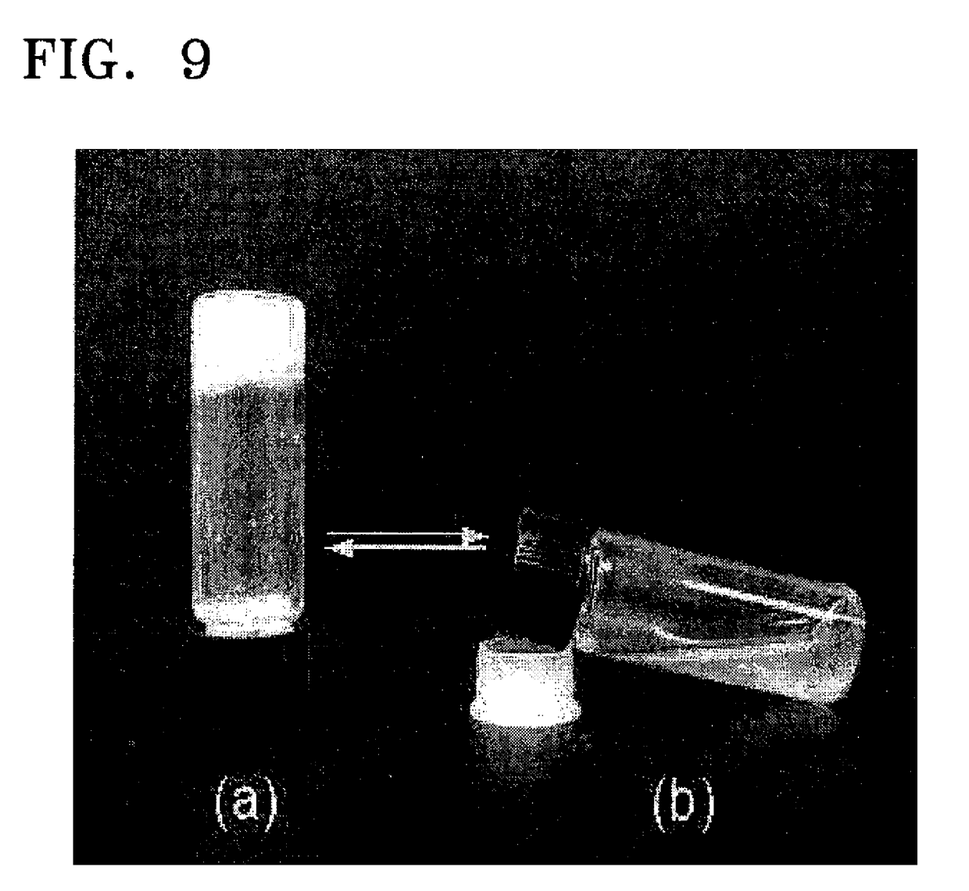
FIG. 9 is images of the sol and gel phases of a composition prepared by dissolving cucurbit[7]uril in a sulfuric acid solution followed by addition of benzoquinone.

In FIG. 9, (b) is an image of a sol obtained by dissolving benzoquinone in a cucurbit[7]uril-containing solution and (a) is an image of a gel obtained through conversion of benzoquinone to hydroquinone when a voltage is applied to the sol of (b).

As described above, according to the present invention, a cucurbituril-containing gel can be prepared by various methods. A gel according to the present invention can include various compounds. According to the characteristics of a compound contained in a gel, a drug-containing gel or a gel capable of undergoing a sol-gel transition in response to an external stimulus can be prepared.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A gel comprising a compound represented by Formula 1 below; and at least one compound selected from the group consisting of a pharmacologically active substance and a stimulus-responsive compound comprising an azobenzene group or a stilbene group:

(1)

wherein n is an integer of 4 to 20;
X is O, S, or NH; and
$A_1$ and $A_2$ are each independently H, OR, SR, or NHR where R is selected from the group consisting of H, substituted or unsubstituted $C_1$-$C_{30}$ alkyl, substituted or unsubstituted $C_2$-$C_{30}$ alkenyl, substituted or unsubstituted $C_2$-$C_{30}$ alkynyl, substituted or unsubstituted $C_2$-$C_{30}$ carbonylalkyl, substituted or unsubstituted $C_1$-$C_{30}$ thioalkyl, substituted or unsubstituted $C_1$-$C_{30}$ alkylthiol, substituted or unsubstituted $C_1$-$C_{30}$ hydroxyalkyl, substituted or unsubstituted $C_1$-$C_{30}$ alkylsilyl, substituted or unsubstituted $C_1$-$C_{30}$ aminoalkyl, substituted or unsubstituted $C_1$-$C_{30}$ aminoalkylthioalkyl, substituted or unsubstituted $C_5$-$C_{30}$ cycloalkyl, substituted or unsubstituted $C_2$-$C_{30}$ heterocycloalkyl, substituted or unsubstituted $C_6$-$C_{30}$ aryl, substituted or unsubstituted $C_6$-$C_{20}$ arylalkyl, substituted or unsubstituted $C_4$-$C_{30}$ heteroaryl, and substituted or unsubstituted $C_4$-$C_{30}$ heteroarylalkyl.

2. The gel of claim 1, wherein $A_1$ or $A_2$ is an allyloxy group.

3. The gel of claim 1, wherein n is 7, X is O, and $A_1$ and $A_2$ are each H.

4. The gel of claim 1, wherein the content of the compound of Formula 1 is 1 to 10 wt %.

5. The gel of claim 1, further comprising an acid.

6. The gel of claim 5, wherein the acid is selected from the group consisting of sulfuric acid, hydrochloric acid, nitric acid, phosphoric acid, chloric acid, $HBF_4$, $HPF_6$, acetic acid, trifluoroacetic acid, oxalic acid, benzoic acid, ascorbic acid, and $HAuCl_4$.

7. The gel of claim 1, further comprising a base.

8. The gel of claim 7, wherein the base is selected from the group consisting of sodium hydroxide, potassium hydroxide, calcium hydroxide, methylamine, ethylamine, pyridine, and aniline.

9. The gel of claim 1, wherein the pharmacologically active substance is an organic compound selected from the group consisting of hydrocortisone, prednisolone, spironolatone, testosterone, megestrol acetate, danasol, progesterone, indometasine, amphotericin B, and a combination thereof.

10. The gel of claim 1, wherein the pharmacologically active substance is a protein selected from the group consisting of human growth hormone, G-CSF (granulocyte colony-stimulating factor), GM-CSF (granulocyte-macrophage colony-stimulating factor), erythropoietin, vaccine, antibody, insulin, glucagon, calcitonin, ACTH (adrenocorticotropic hormone), somatostatin, somatotropin, somatomedin, parathormone, thyroxine, a substance secreted from hypothalamus, prolactin, endorphin, VEGF (vascular endothelial growth factor), enkephalin, vasopressin, nerve growth factor, non-naturally occurring opioid, interferon, asparaginase, alginase, superoxide dismutase, trypsin, chymotrypsin, pepsin, and a combination thereof.

11. The gel of claim 1, wherein the stimulus-responsive compound is quinone, benzoquinone, naphthoquinone, anthraquinone, hydroquinone, catechol, viologen, or a compound comprising one of these.

* * * * *